United States Patent
Moller et al.

(10) Patent No.: US 7,491,371 B2
(45) Date of Patent: Feb. 17, 2009

(54) CONTROL OF STERILIZATION DEVICE AND METHOD

(75) Inventors: Hakan Moller, Lund (SE); Laurence Mott, Trelleborg (SE); Lars Martensson, Veberod (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 282 days.

(21) Appl. No.: 10/531,297

(22) PCT Filed: Nov. 19, 2003

(86) PCT No.: PCT/SE03/01791

§ 371 (c)(1),
(2), (4) Date: Apr. 14, 2005

(87) PCT Pub. No.: WO2004/054882

PCT Pub. Date: Jul. 1, 2004

(65) Prior Publication Data

US 2006/0008383 A1    Jan. 12, 2006

(30) Foreign Application Priority Data

Dec. 13, 2002 (SE) .................................. 0203693

(51) Int. Cl.
*A61L 2/00* (2006.01)
*A61L 2/24* (2006.01)
*G01N 31/00* (2006.01)

(52) U.S. Cl. .............................. 422/292; 422/3; 422/62

(58) Field of Classification Search ................... 422/62, 422/295, 3

See application file for complete search history.

(56) References Cited

U.S. PATENT DOCUMENTS 3,891,779 A * 6/1975 Robinson ..................... 426/399

(Continued)

FOREIGN PATENT DOCUMENTS

EP          0 394 734 B1      10/1990

(Continued)

OTHER PUBLICATIONS

"Betriebsanleitung combibloc-Fümaschine CFA 510-32" (Technical Manual of FCA 510 Combibloc Machine), Feb. 8, 2002, SIC Combibloc GmbH, Linnich, Germany, (p. 6-124, paragraph 2; p. 6-124, paragraph 4; and p. 6-106, last paragraph).

(Continued)

*Primary Examiner*—Elizabeth L McKane
*Assistant Examiner*—Kevin C Joyner
(74) *Attorney, Agent, or Firm*—Buchanan, Ingersoll & Rooney PC

(57) ABSTRACT

A device (1) for sterilization in production of packages (8) is adapted for sterilization with a gaseous sterilizing agent kept in the gaseous phase throughout the sterilization process. The device (1) comprises a heating zone (2), a sterilization zone (3) and a venting zone (4). It further comprises an ambient temperature sensor (27) for sensing the ambient temperature outside the device (1), a concentration meter (29) for measuring the concentration of sterilizing agent in the sterilization zone (3) and a first control unit for controlling the amount of sterilizing agent introduced in the sterilization zone (3) based on the temperature measured by the ambient temperature sensor (27) and the concentration measured by the concentration meter (29). A method of sterilizing packages (8) in production of the packages (8) is also disclosed.

27 Claims, 2 Drawing Sheets

U.S. PATENT DOCUMENTS

| | | | |
|---|---|---|---|
| 4,979,347 A * | 12/1990 | Shibauchi et al. | 53/167 |
| 5,258,162 A | 11/1993 | Andersson et al. | |
| 5,697,203 A * | 12/1997 | Niwa | 53/510 |
| 5,906,794 A | 5/1999 | Childers | |
| 2001/0000558 A1 * | 5/2001 | Taggart | 53/138.1 |
| 2002/0159915 A1 * | 10/2002 | Zelina et al. | 422/3 |
| 2003/0103864 A1 * | 6/2003 | McAffer et al. | 422/1 |

FOREIGN PATENT DOCUMENTS

| | | | | |
|---|---|---|---|---|
| GB | 2354443 A * | 3/2001 | | 422/26 |
| WO | WO 01/07092 | 2/2001 | | |

OTHER PUBLICATIONS

"Bericht über die Typprüfung der aseptischen Füllmaschine Typ CFA 510" Institut für Lebensmittel-verfahrenstechnik, Weihenstephan, Germany, Nov. 15, 1999.

Article in "Verpackungs-Rundschau" Mar. 1998.

H.W. Knuppertz, "Konstruktive Anforderungen an Aseptikanlagen" Seminar Oct. 22-23, 1987, Munich, Germany.

H.G. Kessler: "Prüfung der abpackmaschine Typ combibloc aseptic—Füller cF 5.000 zur Abpackung ultrahocherhitzter Milch," "Die Molkerei-Zeitung Welt Der Milch," Nr. 5/1977. Hersteller: Jagenberg-Werke AB, Düsseldorf, Germany.

* cited by examiner

CONTROL OF STERILIZATION DEVICE AND METHOD

TECHNICAL FIELD OF THE INVENTION

The present invention relates to a device for sterilization in production of packages, which is adapted for sterilization with a gaseous sterilizing agent kept in the gaseous phase throughout the sterilization process, said device comprising a heating zone, a sterilization zone and a venting zone. The present invention also relates to a method of sterilizing packages in production of the packages, said packages having an open end and a closed end, wherein a gaseous sterilizing agent is used and kept in the gaseous phase throughout the sterilization process.

BACKGROUND ART

Devices and methods of the above-mentioned kind are known in the art, e.g. from U.S. Pat. No. 5,258,162. Here, packages are passed through a housing divided into zones. In the first zone, hot air is introduced for heating the packages. In the second zone, gaseous hydrogen-peroxide is introduced for sterilizing the heated packages. In the third and final zone, the packages are filled with sterile contents. The three zones are all contained in one housing and are not physically separated from each other. Therefore, it may be difficult to control the flow between the different zones.

EP-A-394 734 discloses another device and method for sterilizing objects. In the device and method described, a vertically displaceable hood is placed over the object to be sterilized. A negative pressure is produced in the hood and a sterilization gas is introduced. The fact that a displaceable hood is needed makes this device somewhat complex.

SUMMARY OF THE INVENTION

An object of the present invention is to provide a device for sterilizing packages essentially of the type described above, but which enables an even safer sterilization process.

A specific object of the invention is to provide a device which allows improved control of the gas flow in and between the different zones.

Another object is to provide a device which allows improved control of the heating of packages.

It is also an object of the present invention to provide a method of sterilizing packages, which is improved as compared to prior art methods.

Yet another object is to provide a method which allows better control of the flow of air and gas in and between the different zones where the sterilization takes place.

According to the invention, these objects are achieved by a device of the kind mentioned by way of introduction, which has been given characteristics disclosed herein. Preferred embodiments of the inventive device are also disclosed.

The above-mentioned objects are also achieved by a method disclosed herein.

The inventive device for sterilization in production of packages comprises an ambient temperature sensor for sensing the ambient temperature outside the device, a concentration meter for measuring the concentration of sterilizing agent in the sterilization zone and a first control unit for controlling the amount of sterilizing agent introduced in the sterilization zone based on the temperature measured by the ambient temperature sensor and the concentration measured by the concentration meter. This makes it possible to achieve improved control of the sterilization process.

In a preferred embodiment, the device comprises means for maintaining a higher pressure in the sterilization zone than in the heating zone and venting zone. Thus, it is possible to ensure that any leakage of air and gas is from the sterilization zone towards the surrounding zones and not the other way round.

In one embodiment, the heating, sterilization and venting zones are separated from each other by means of partitionings having openings for the passage of packages. This makes it easier to control the conditions in each zone.

The device is preferably adapted for sterilization with a gaseous sterilizing agent in the form of gaseous hydrogen peroxide. Hydrogen peroxide is a useful and reliable sterilizing agent.

The device is preferably adapted to sterilize packages before filling of the packages, said packages having an open end and a closed end. It is convenient to sterilize packages before filling them, since this makes it possible to maintain the sterility of sterile contents.

The heating zone may comprise means for heating the packages to a temperature above a dew point of the sterilizing agent used in the sterilization zone. In this way, it may be ensured that the sterilizing agent does not condensate on the packages.

In one embodiment, the venting zone comprises means for venting away the sterilizing agent used in the sterilization zone from the packages after sterilization. This makes it possible to ensure that the packages are free from sterilizing agent before filling.

The device may further comprise means for controlling a flow of gaseous sterilizing agent in the sterilization zone, such that the gaseous sterilizing agent flows essentially in a direction from the open end of the packages towards the closed end of the packages. This reduces the risk of recontamination of the packages.

The means for controlling the flow of gaseous sterilizing agent are preferably arranged to introduce the gaseous sterilizing agent in a top portion of the sterilization zone and to evacuate the gaseous sterilizing agent in a bottom portion of the sterilization zone, maintaining a flow of gaseous sterilizing agent essentially from top to bottom. This provides a secure way of maintaining a flow from the open end of the packages towards the closed end of packages standing on their closed end.

The device may further comprise means for controlling a venting air flow in the venting zone, such that the venting air flows essentially in a direction from the open end of the packages towards the closed end of the packages. Thus, the risk of recontamination of the sterilized packages may be reduced.

The means for controlling the flow of venting air are arranged to introduce the venting air in a top portion of the venting zone and to evacuate the venting air in a bottom portion of the venting zone, maintaining a flow of venting air essentially from top to bottom.

In one embodiment of the invention, the device comprises an ambient temperature sensor for sensing the ambient temperature outside the device. In this way, the heating in the heating zone may be controlled based on the ambient temperature.

Alternatively or additionally, the device may comprise a package heating temperature sensor for sensing the temperature of the packages entering the heating zone. This may also be used for controlling the heating.

In another embodiment, the device comprises an entry temperature sensor for sensing the temperature of the packages before entry into the sterilization zone. This is another way of enabling control of the heating in the heating zone.

In a preferred embodiment of the invention, the device comprises a feedback circuit for controlling the heating in the heating zone based on the temperature of the packages. In this way, heating to a correct temperature may be ensured and over-heating of the packages may be avoided.

In another embodiment, the device further comprises a condensation detector for detecting condensation in the sterilization zone. Thus, it is possible to mark or discard packages that have been subjected to condensate.

The device of the invention is preferably adapted to sterilize itself internally. Thus, sterile conditions in the device may be ensured in a simple manner.

For sterilizing itself, the device preferably comprises means for heating its interior. This allows efficient sterilization.

The inventive device may comprise a unit for production of the gaseous sterilizing agent, thus making the device self-supporting.

The device may further comprise a filling zone for filling vented packages, and means for maintaining a higher pressure in the filling zone than in the venting zone. This makes it possible to further control the flow of air and gas in the device.

In the method according to the invention for sterilizing packages in production of the packages, said packages having an open end and a closed end, a gaseous sterilizing agent is used and kept in the gaseous phase throughout the sterilization process. An ambient temperature and a concentration of sterilizing agent in a sterilization zone where sterilization is performed are measured and used for controlling the amount of sterilizing agent introduced in the sterilization zone. This makes it possible to achieve improved control of the sterilization process.

In a preferred variant of the method, a positive pressure is maintained in the sterilization zone in which the sterilization is performed.

Gaseous hydrogen peroxide is preferably used as sterilizing agent. This is a well-known and reliable sterilizing agent.

In a variant of the method, the packages are passed into a heating zone where they are heated to a temperature above the dew point of the sterilizing agent. This makes it possible to ensure that the sterilizing agent does not condensate on the packages.

The heated packages may be passed through an opening in a partitioning separating the heating zone and the sterilization zone into the sterilization zone, where they are subjected to the gaseous sterilizing agent. Since the package has to be passed through a partitioning for entering the sterilization zone, it is easier to control the conditions for sterilization.

Analogously, the sterilized packages may be passed through an opening in a partitioning separating the sterilization zone and a venting zone into the venting zone, where they are subjected to hot sterile air for venting away the sterilizing agent. Thus, the packages may be subjected to distinctly different conditions during sterilization and venting.

The gaseous sterilizing agent in the sterilization zone preferably flows essentially in a direction from the open end of the packages towards the closed end of the packages. Thus, the risk of recontamination of packages may be reduced.

The gaseous sterilizing agent may be introduced in a top portion of the sterilization zone and evacuated in a bottom portion of the sterilization zone, so that a flow of sterilizing agent essentially from top to bottom is maintained. This is a simple way of maintaining a suitable flow for packages standing on their closed end.

In one variant of the method, the venting air in the venting zone flows essentially in a direction from the open end of the packages towards the closed end of the packages. As in the case in the sterilization zone, this reduces the risk of recontamination of packages.

The venting air is preferably introduced in a top portion of the venting zone and evacuated in a bottom portion of the venting zone, so that an air flow essentially from top to bottom is maintained. This is a simple manner of ensuring a suitable flow for packages standing on their closed end.

In a preferred variant of the method, the gaseous sterilizing agent is produced by addition of liquid sterilizing agent to hot air. Thus, the sterilization process may simply and reliably be provided with gaseous sterilizing agent.

An ambient temperature and a concentration of sterilizing agent in the sterilization zone may be measured for controlling the amount of sterilizing agent introduced the sterilization zone.

An ambient temperature may be measured and used for controlling the heating in the heating zone, thus improving control of the sterilization process.

In a variant of the method, a temperature of the packages entering the heating zone is measured and used for controlling the heating in the heating zone. This is an alternative or additional manner of controlling the conditions for the sterilization process.

Further, a temperature of the packages just before they are passed into the sterilization zone may be measured and used for controlling the heating in the heating zone. This is another convenient way of controlling the conditions for the sterilization process.

In one variant of the method of the invention, the temperature and flow of air for production of the gaseous sterilizing agent is controlled based on detection of condensation in the sterilization zone. This makes it easier to avoid condensation.

A higher pressure is preferably maintained in a filling zone for filling vented packages than in the venting zone. Thus, control of flow between the different zones may be improved.

BRIEF DESCRIPTION OF THE DRAWINGS

The invention will be described in more detail with reference to the appended schematic drawings, which show an example of a currently preferred embodiment of the invention.

DETAILED DESCRIPTION OF PREFERRED EMBODIMENTS

Figure 1:
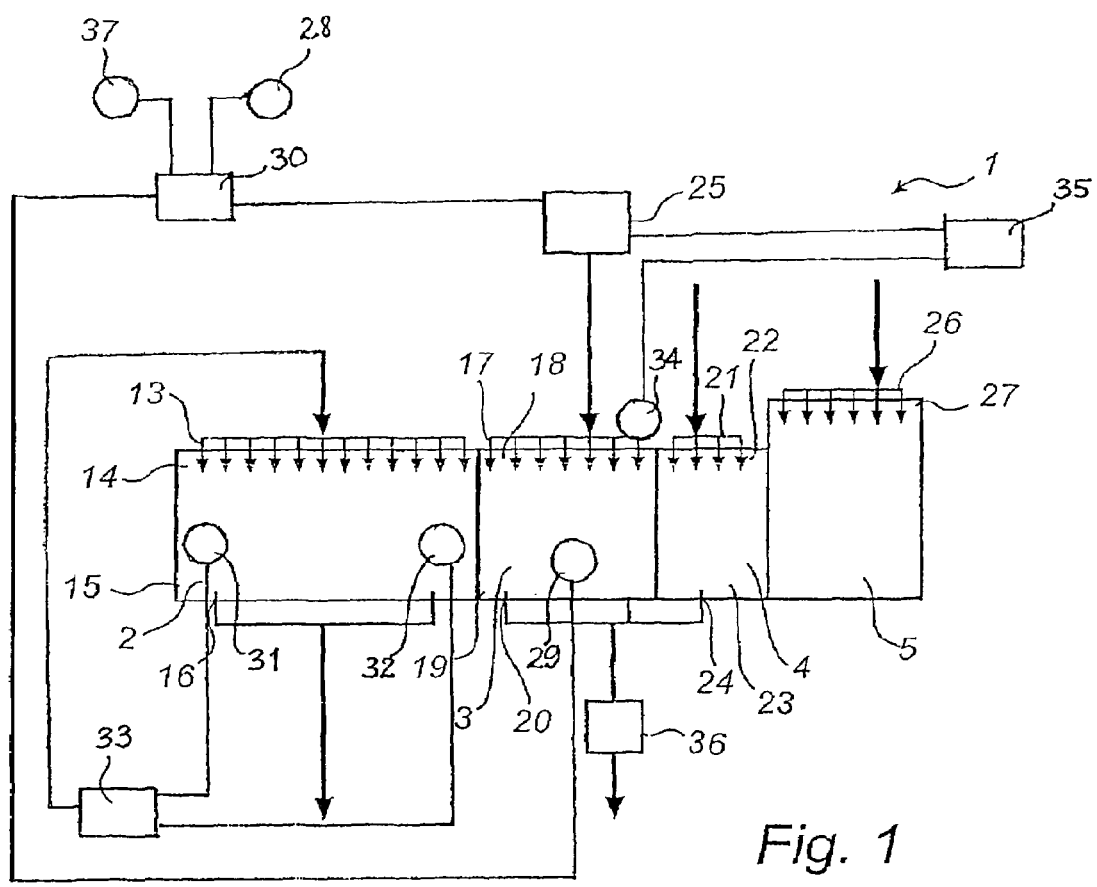
FIG. 1 is a diagram showing the principles of the sterilizing device of the invention.
Figure 2:
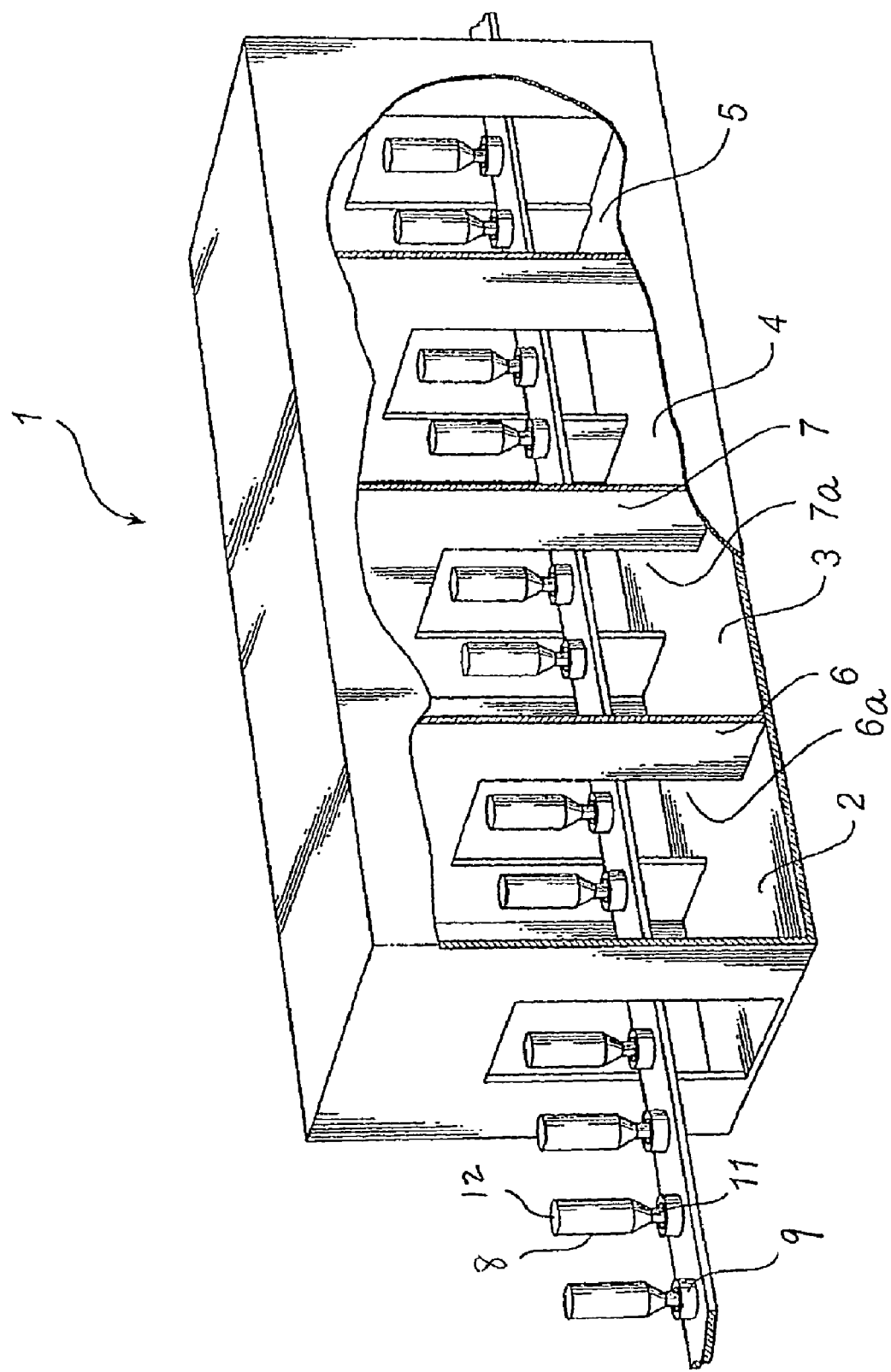
FIG. 2 is a perspective view of the sterilizing device.

With reference to FIG. 1, the sterilization device 1 has a heating zone 2, a sterilization zone 3, a venting zone 4 and connected thereto a filling zone 5. As may be seen from FIG. 2, the zones 2-5 are separated from each other by partitionings 6-7. In each partitioning 6, 7 there is an opening 6a, 7a. Packages 8 are arranged in holders 9 on a conveyor belt 10 which passes through the zones 2-5. The packages 8 stand on their closed top end 11 with their open bottom end 12 directed upwards.

In the heating zone 2 there are nozzles 13 in a top portion 14 for introduction of hot sterile air. In a bottom portion 15 of the heating zone 2 there are outlets 16 for withdrawing the hot air.

Similarly, there are nozzles 17 for introduction of gaseous hydrogen peroxide in a top portion 18 of the sterilization zone 3. In a bottom portion 19 of the sterilization zone there are outlets 20 for withdrawing hydrogen peroxide.

The venting zone 4 also has nozzles 21 for introducing hot sterile air in a top portion 22. In a bottom portion 23 of the venting zone 4 there are outlets 24 for withdrawing hot air.

The sterilizing device has a gas production unit 25 for producing the gaseous hydrogen peroxide used for sterilization.

In a manner similar to the heating, sterilization and venting zones 2-4, the filling zone 5 has nozzles 26 for introducing sterile air in a top portion 27 of the filling zone.

Included in the device 1 is further a catalyst unit 36 for degrading hydrogen peroxide gas withdrawn from the sterilization zone 3.

The method by which packages are treated in this device 1 will now be described. A package 8 standing on its closed top end 11 in one of the holders 9 is transported by the conveyor belt 10 into the heating zone 2. Here, sterile air with a temperature of approximately 140° C. is introduced in the top portion 14 by means of the nozzles 13. In this manner the package 8 is heated to a temperature above the dew point of the gaseous sterilizing agent to be used in the sterilization zone 3. Thus, it may be ensured that hydrogen peroxide does not condensate on the package 8. The temperature to which the package 8 should be heated depends on the content of hydrogen peroxide in the sterilizing gas, but is normally approximately 70° C.

Since the heating air is introduced in the top portion 14 of the heating zone 2 and withdrawn through the outlets 16 in the bottom portion 15, an air flow essentially from top to bottom of the heating zone 2 is ensured. Thus, it is also ensured that air flows past the package 8 from the open end 11 towards the closed end 12. This one-way air flow reduces the risk of particles and micro organisms whirling about in the heating zone 2.

Heating in the heating zone 2 is controlled based on a temperature measured on the inside of the package 8 by means of a package heating temperature sensor 31, e.g. an IR temperature sensor. This package heating temperature sensor 31 may also be used in a feed-back circuit providing a safety device for the heating. If, for instance, the conveyor belt 10 transporting the packages is stopped, continued heating in the heating zone 2 might lead to melting of e.g. plastic lids on the packages 8. Therefore, if a predetermined high temperature is measured by the inside temperature sensor, hot air will be by-passed via a shunt, thus not raising the temperature in the heating zone further. When a predetermined low temperature is measured, heating in the heating zone 2 recommences. The predetermined high and low temperature levels are determined based on the properties of the material in the packages 8 and on the hydrogen peroxide content of the sterilizing gas.

The heated package 8 is passed by the conveyor belt 10 through the opening 6a in the partitioning or semi-open wall 6 into the sterilization zone 3. Here, the package 8 is subjected to gaseous hydrogen peroxide introduced at a temperature of approximately 95° C. in the top portion 18 via the nozzles 17. The hydrogen gas is withdrawn through the outlets 20 in the bottom portion 19 and therefore a one-way gas flow is maintained from the top of the sterilization zone 3 towards the bottom. This also means that the flow past the packages 8 is directed from the open end 12 towards the closed end 11. This reduces the risk of recontamination of the packages 8.

Further, an accurate sterilization may be achieved both of the inside and the outside of the package 8. Sterilization of the inside of the package 8 is essential in order to maintain sterility of sterile contents subsequently filled in the package 8. Sterility of the outside of the package improves manageability of the package 8, since the package 8 may be displaced vertically for moving towards and away from an injection nozzle during filling of the package 8 without the risk of particles or micro organisms on the outside of the package 8 contaminating the inside.

Gaseous hydrogen peroxide is introduced and withdrawn at such rate that a positive pressure is maintained in the sterilization zone 3. Thus, it may be ensured that any leakage of gas and air between the sterilization zone 3 and the surrounding heating and venting zones 2, 4 is from the sterilization zone 3 towards the surrounding zones 2, 4. This improves the conditions for an accurate sterilization. Approximately 20% of the gas leaving the sterilization zone 3 will seep into the heating and venting zones 2, 4, the remaining 80% being withdrawn through the outlets 20.

The sterilizing gas used in the sterilization zone 3 is produced in the gas production unit 25 by addition of liquid hydrogen peroxide to hot sterile air. The desired hydrogen peroxide concentration in the sterilizing agent may be adjusted by adjustment of the proportion of liquid hydrogen peroxide added to the air. In the example shown, a sterilizing gas containing approximately 35% hydrogen peroxide is used for sterilization of packages.

Gas withdrawn through the outlets 20 in the bottom portion 19 of the sterilization zone 3 is passed through the catalyst unit 36 for removing hydrogen peroxide from the gas before being evacuated through the evacuation system of the device 1.

The fact that the package 8 is heated above the dew point of the hydrogen peroxide gas before entry into the sterilization zone 3 ensures that hydrogen peroxide does not condensate on the package 8. Therefore, removal of hydrogen peroxide from the package through venting in the venting zone 4 is facilitated. This allows a reliable sterilization even of packages with difficult geometries, e.g. with crevices and pores, without the risk of high residuals of hydrogen peroxide on the package 8 to be filled with an edible content.

The sterilized package 8 is passed through the opening 7a in the partitioning or semi-open wall 7 into the venting zone 4. In the venting zone 4, sterile air is introduced via the nozzles 21 in the top portion 22 at a temperature of approximately 70° C. The venting air vents away hydrogen peroxide remaining in and on the package 8. Venting is facilitated by the fact that the heating of the package 8 has eliminated condensation of hydrogen peroxide on the package.

The package 8, now sterilized and essentially free from residual hydrogen peroxide, is passed into the filling zone 5 where it is filled with a sterile content, e.g. milk, juice or tomato paste. In order to ensure an air flow essentially from top to bottom, thus minimizing the risk of recontamination of the package 8, sterile air is introduced via the nozzles 26 in the top portion 27 of the filling zone 5. A positive pressure is maintained in the filling zone 5, such that air flow is from the filling zone 5 outwards and not the other way round.

The filled package 8 is then transported on for sealing and folding of the bottom.

The partitionings between the different zones 2-5 make it possible to control the conditions in each separate zone 2-5 and to control the flow between zones 2-5.

When a production run is finished or when a new run is to begin, the device itself needs to be sterilized. Hot sterile air is then introduced via the nozzles 13 in the heating zone 2 and the inside of the device 1 is heated to approximately 35° C. When the interior has reached the appropriate temperature, gaseous hydrogen peroxide is introduced in the entire device via the nozzles 17 in the sterilization zone 3. The flow pattern will be different during machine sterilization, i.e. sterilization of the interior of the device 1, as compared to during package sterilization, since the entire interior is to be heated and sterilized. As with package sterilization, sterilizing gas is withdrawn via the catalyst unit 36 for destruction of the hydrogen peroxide.

The sterilization process in the device of the invention is controlled by means of three control loops. In the first control loop, an ambient temperature sensor 37 measures the temperature outside the device 1 and a relative humidity sensor 28 measures the relative humidity outside the device. A concentration meter 29 measures the hydrogen peroxide concentration in the sterilization zone 3. A first control unit 30 receives signals from the ambient temperature sensor 37, the relative humidity sensor 28 and the concentration meter 29 and regulates the amount of hydrogen peroxide added in production of the sterilizing gas. During machine sterilization, the data from the temperature sensor 37, relative humidity sensor 28 and the concentration meter 29 are used for regulating the amount of hydrogen peroxide added to the air stream in the gas production unit 25. In this manner, optimal conditions may be achieved for machine sterilization. During package sterilization, when the hydrogen peroxide concentration of the sterilizing gas is normally significantly higher than during machine sterilization, the relative humidity outside the device 1 is not as important, and therefore only the ambient temperature sensor 37 and the concentration meter 29 are used for regulating the hydrogen peroxide amount added in the gas production unit 25. In this manner, the killing efficiency of the gas may be controlled for purposes of package sterilization.

In the second control loop, a the package heating temperature sensor 31 is used for measuring the temperature of the packages 8 before entering the device (i.e., start) and a package heating temperature sensor 32 is used for measuring the temperature of the packages 8 just before they leave the heating zone 2. Signals from these two temperature sensors 31, 32 are sent to a second control unit 33 which regulates the temperature of the hot air introduced in the heating zone 2 for heating the packages 8 to the required temperature above the dew point of the sterilizing gas. Thus, a correct temperature of the packages 8 may be ensured before they enter the sterilization zone 3.

In the third control loop, a condensation detector 34 detects possible occurrence of condensation in the sterilization zone 3. A signal from the condensation detector 34 is sent to a third control unit 35. If condensation is detected, a signal is sent from the third control unit 35 and used for controlling the temperature and/or flow of hot air in the gas production unit 25. Thus, the temperature of the sterilizing gas and/or the hydrogen peroxide content may be adjusted, such that condensation is avoided. Further, if condensation has been detected, it is possible to mark or discard the packages concerned.

The skilled person will realise that a number of modifications of the invention described above are possible without departing from the scope of the invention as defined in the appended claims.

For instance, only the first of the three control loops described above could be used, or the first control loop could be used in combination with one of the two other control loops.

This first control loop may also be supplemented with a flow meter (not shown) measuring the air flow to the gas production unit connected to the first control unit 30. If the flow of air into the gas production unit 25, and thereby into the sterilization chamber 3, is reduced, e.g. if a filter in the air duct is clogged, the hydrogen peroxide concentration in the sterilizing gas and thus in the sterilization chamber 3 will rise. The first control loop would in such case regulate the amount of hydrogen peroxide added in gas production downwards. However, this may lead to too small a gas flow, so that not all parts of the packages are reached by the sterilizing gas. Therefore, the first control unit 30 may be arranged to sound an alarm at a predetermined low-level flow, so that the low flow may be corrected instead of just lowering the amount of hydrogen peroxide added in the sterilizing gas. Similarly, an alarm signal may be sent at a predetermined high-level flow.

Other means of controlling the heating in the heating zone 2 may also be used. The ambient temperature sensor 37 may be used for determining the temperature outside the device 1. With knowledge of the properties of the materials in the package 8, the required temperature and flow of hot air introduced through the nozzles 13 may be calculated. This may also be combined with the package heating temperature sensor 32 described above for better control and for providing a safety feature.

The package heating temperature sensor 32 may be arranged in the holders 9 holding the packages for measuring the temperature of the packages 8 just before they enter the sterilization zone 3. This temperature sensor 32 may be used for controlling the temperature and flow of the heating air as well as for controlling the safety shunt. It may also be combined with one or both of the previously described temperature sensors for allowing even better control of the heating.

Other sterilizing agents than hydrogen peroxide may also be used, as long as they are suitable for sterilization in the gaseous phase.

The invention claimed is;

1. A device for sterilization in production of packages, which is adapted for sterilization with a gaseous sterilizing agent kept in the gaseous phase throughout the sterilization process, said device comprising a heating zone, a sterilization zone, a venting zone, an ambient temperature sensor located outside of the device for sensing the ambient temperature outside the device where the sterilizing agent does not flow, a relative humidity sensor for measuring the relative humidity outside the device where the sterilizing agent does not flow, a concentration meter for measuring the concentration of sterilizing agent in the sterilization zone, and a first control unit for controlling the amount of sterilizing agent introduced in the sterilization zone based on the temperature measured by the ambient temperature sensor, the relative humidity measured by the relative humidity sensor and the concentration measured by the concentration meter.

2. A device as claimed in claim 1, further comprising a package start temperature sensor for sensing the temperature of the packages entering the heating zone.

3. A device as claimed in claim 1, further comprising a package heating temperature sensor for sensing the temperature of the packages before entry into the sterilization zone.

4. A device as claimed in claim 1, further comprising a feedback circuit for controlling the heating in the heating zone based on the temperature of the packages.

5. A device as claimed in claim 1, further comprising a condensation detector for detecting condensation in the sterilization zone.

6. A device as claimed in claim 5, further comprising a third control unit in communication with the condensation detector, wherein the third control unit is operable to send a signal to control the temperature and/or flow of hot air in a gas production unit which produces the sterilizing agent.

7. A device as claimed in claim 1, further comprising means for maintaining a higher pressure in the sterilization zone than in the heating zone and venting zone.

8. A device as claimed in claim 1, wherein said zones are separated from each other by means of partitionings having openings for the passage of packages.

9. A device as claimed in claim 1, which is adapted for sterilization with a gaseous sterilizing agent in the form of gaseous hydrogen peroxide.

10. A device as claimed in claim 1, which is adapted to sterilize packages having an open end and a closed end, wherein the sterilized packages are subjected to filling.

11. A device as claimed in claim 10, wherein the heating zone comprises means for heating the packages to a temperature above a dew point of the sterilizing agent used in the sterilization zone.

12. A device as claimed in claim 10, wherein the venting zone comprises means for venting away the sterilizing agent used in the sterilization zone from the packages after sterilization.

13. A device as claimed in claim 10, further comprising means for controlling a flow of gaseous sterilizing agent in the sterilization zone, such that the gaseous sterilizing agent flows essentially in a direction from the open end of the packages towards the closed end of the packages.

14. A device as claimed in claim 13, wherein the means for controlling the flow of gaseous sterilizing agent are arranged to introduce the gaseous sterilizing agent in a top portion of the sterilization zone and to evacuate the gaseous sterilizing agent in a bottom portion of the sterilization zone, maintaining a flow of gaseous sterilizing agent essentially from top to bottom.

15. A device as claimed in claim 14, further comprising:
nozzles in fluid communication with the unit for production of the gaseous sterilizing agent, wherein the nozzles are arranged to introduce the gaseous sterilizing agent in a top portion of the sterilization zone; and
outlets in a bottom portion of the sterilization zone for withdrawing the gaseous sterilizing agent from the sterilization zone.

16. A device as claimed in claim 15, further comprising a catalyst unit in fluid communication with outlets in a bottom portion of the sterilization zone for degrading the gaseous sterilizing agent withdrawn from the sterilization zone.

17. A device as claimed in claim 15, wherein the first control unit controls the operation of the unit for production of the gaseous sterilizing agent.

18. A device as claimed in claim 10, further comprising means for controlling a venting air flow in the venting zone, such that the venting air flows essentially in a direction from the open end of the packages towards the closed end of the packages.

19. A device as claimed in claim 18, wherein the means for controlling the flow of venting air are arranged to introduce the venting air in a top portion of the venting zone and to evacuate the venting air in a bottom portion of the venting zone, maintaining a flow of venting air essentially from top to bottom.

20. A device as claimed in claim 1, which is adapted to sterilize itself internally.

21. A device as claimed in claim 20, further comprising means for heating the interior of the device.

22. A device as claimed in claim 1, comprising a unit for production of the gaseous sterilizing agent.

23. A device as claimed in claim 1, further comprising a filling zone for filling packages, and means for maintaining a higher pressure in the filling zone than in the venting zone.

24. A device as claimed in claim 23, further comprising:
nozzles arranged to introduce sterile air in a top portion of the filling zone; and
outlets in a bottom portion of the filling zone for withdrawing the sterile air from the filling zone.

25. A device as claimed in claim 1, further comprising:
nozzles arranged to introduce hot sterile air in a top portion of the heating zone; and
outlets in a bottom portion of the heating zone for withdrawing the sterile air.

26. A device as claimed in claim 25, further comprising a second control unit for regulating the temperature of the hot sterile air introduced into the heating zone to heat packages therein to a temperature above a dew point of the sterilizing agent.

27. A device as claimed in claim 1, further comprising:
nozzles arranged to introduce sterile air in a top portion of the venting zone; and
outlets in a bottom portion of the venting zone for withdrawing the sterile air from the venting zone.

* * * * *